United States Patent
Lim et al.

(10) Patent No.: US 8,404,461 B2
(45) Date of Patent: Mar. 26, 2013

(54) METHOD FOR PREPARATION OF CARBAMIC ACID (R)-1-ARYL-2-TETRAZOLYL-ETHYL ESTER

(75) Inventors: Sang Chul Lim, Daejeon (KR); Moo Yong Uhm, Daejeon (KR); Dae Won Lee, Siheung-si (KR); Hui Ho Kim, Daejeon (KR); Dong Ho Lee, Daejeon (KR); Hyun Seok Lee, Daejeon (KR)

(73) Assignee: SK Biopharmaceutical Co. Ltd., Seoul (KR)

( * ) Notice: Subject to any disclaimer, the term of this patent is extended or adjusted under 35 U.S.C. 154(b) by 141 days.

(21) Appl. No.: 12/904,267

(22) Filed: Oct. 14, 2010

(65) Prior Publication Data

US 2011/0111467 A1 May 12, 2011

Related U.S. Application Data

(60) Provisional application No. 61/251,867, filed on Oct. 15, 2009.

(51) Int. Cl.
*C12P 1/00* (2006.01)

(52) U.S. Cl. .............. 435/41; 435/84; 435/135; 435/155

(58) Field of Classification Search ........................ None
See application file for complete search history.

(56) References Cited

U.S. PATENT DOCUMENTS

| | | | |
|---|---|---|---|
| 5,276,154 A | 1/1994 | Hiyama et al. | |
| 5,391,495 A | 2/1995 | Patel et al. | |
| 5,393,663 A | 2/1995 | Patel et al. | |
| 5,523,223 A | 6/1996 | Kula et al. | |
| 6,218,156 B1 | 4/2001 | Hasegawa et al. | |
| 6,225,099 B1 | 5/2001 | Hummel et al. | |
| 6,255,087 B1 | 7/2001 | Dingler et al. | |
| 6,255,092 B1 | 7/2001 | Kojima et al. | |
| 6,416,986 B1 | 7/2002 | Kimoto et al. | |
| 6,645,746 B1 | 11/2003 | Hasegawa et al. | |
| 6,800,477 B2 | 10/2004 | Patel et al. | |
| 6,969,600 B2 | 11/2005 | Kimoto et al. | |
| 7,056,540 B2 | 6/2006 | Nanda et al. | |
| 7,083,962 B2 | 8/2006 | Kimoto et al. | |
| 7,172,894 B2 | 2/2007 | Ito et al. | |
| 7,332,312 B2 | 2/2008 | Kizaki et al. | |
| 7,335,757 B2 | 2/2008 | Hiraoka et al. | |
| 7,371,903 B2 | 5/2008 | Gupta et al. | |
| 7,446,187 B2 | 11/2008 | Yamamura et al. | |
| 7,575,909 B2 | 8/2009 | Gupta et al. | |
| 2002/0042110 A1 | 4/2002 | Kimoto et al. | |
| 2003/0032153 A1 | 2/2003 | Yamamoto et al. | |
| 2003/0054520 A1 | 3/2003 | Bommanus et al. | |
| 2003/0130521 A1 | 7/2003 | Amano et al. | |
| 2004/0197773 A1 | 10/2004 | Kimoto et al. | |
| 2004/0265978 A1 | 12/2004 | Gupta et al. | |
| 2005/0003500 A1 | 1/2005 | Kudo et al. | |
| 2005/0202545 A1 | 9/2005 | Ishihara et al. | |
| 2005/0227336 A1 | 10/2005 | Yamamoto et al. | |
| 2006/0177913 A1 | 8/2006 | Peschko et al. | |
| 2006/0211099 A1 | 9/2006 | Althofer et al. | |
| 2006/0258718 A1 | 11/2006 | Choi et al. | |
| 2007/0212766 A1 | 9/2007 | Pfaller et al. | |
| 2008/0038803 A1 | 2/2008 | Hasegawa et al. | |
| 2008/0153140 A1 | 6/2008 | Gupta et al. | |
| 2008/0206824 A1 | 8/2008 | Sturmer et al. | |
| 2008/0220484 A1 | 9/2008 | Breuer et al. | |
| 2008/0233621 A1 | 9/2008 | Dekishima et al. | |
| 2008/0261286 A1 | 10/2008 | Ishihara et al. | |
| 2009/0017510 A1 | 1/2009 | Gupta et al. | |
| 2009/0029430 A1 | 1/2009 | Kizaki et al. | |
| 2009/0148917 A1 | 6/2009 | Gupta et al. | |
| 2009/0162893 A1 | 6/2009 | Daussmann et al. | |
| 2009/0186391 A1 | 7/2009 | Nishiyama et al. | |
| 2009/0203096 A1 | 8/2009 | Hayashi et al. | |
| 2010/0323410 A1* | 12/2010 | Lim et al. ..................... | 435/121 |

FOREIGN PATENT DOCUMENTS

| | | |
|---|---|---|
| CA | 2625834 | 2/2007 |
| CA | 2621306 | 4/2007 |
| CA | 2633583 | 7/2007 |
| CA | 2671319 | 6/2008 |
| CN | 101314787 | 12/2008 |
| CN | 101319236 | 12/2008 |
| CN | 101358183 | 2/2009 |
| DE | 102004037669 | 3/2005 |
| DE | 102006055047 | 5/2008 |
| JP | 61134339 | 6/1986 |
| JP | 07059592 | 3/1995 |
| JP | 10094399 | 4/1998 |
| JP | 10248591 | 9/1998 |
| JP | 10287634 | 10/1998 |
| JP | 11130761 | 5/1999 |
| JP | 2003289895 | 10/2003 |
| JP | 2004267130 | 9/2004 |
| JP | 2004313033 | 11/2004 |
| JP | 2005006552 | 1/2005 |
| JP | 2007061065 | 3/2007 |
| JP | 2008017773 | 2/2008 |
| PL | 177372 | 11/1999 |
| WO | 9407888 | 4/1994 |
| WO | 2005049816 | 6/2005 |

(Continued)

OTHER PUBLICATIONS

The European Search Opinion mailed Oct. 22, 2012 from the European Patent Office in the corresponding European Patent Application No. 09846577.6.

Hobuss et al., "Catalytic enantioselective borane reduction of arylketones with pinene-derived amino alcohols," Tetrahedron, vol. 64, Issue 8, Feb. 18, 2008, pp. 1635-1640.

D2: Yadav et al., "A facile synthesis of (R)-(−)-2-azido-1-arylethanols from 2-azido-1-arylketones using baker's yeast," Tetrahedron: Asymmetry (Feb. 2001), 12 (1), p. 63-67.

(Continued)

*Primary Examiner* — Nashaat Nashed

(57) ABSTRACT

Disclosed is a method for the preparation of carbamic acid (R)-1-aryl-2-tetrazolyl-ethyl esters, comprising the enantioselective enzyme reduction of a 1-aryl-2-tetrazolyl-ethyl ketone to form a (R)-1-aryl-2-tetrazolyl-ethyl alcohol and the carbamation of said alcohol.

21 Claims, No Drawings

FOREIGN PATENT DOCUMENTS

| | | |
|---|---|---|
| WO | 2005108592 | 11/2005 |
| WO | 2006061137 | 6/2006 |
| WO | 2006094945 | 9/2006 |
| WO | 2006130657 | 12/2006 |
| WO | 2007099764 | 9/2007 |
| WO | 2007099994 | 9/2007 |
| WO | 2008035187 | 3/2008 |
| WO | 2008064817 | 6/2008 |
| WO | 2008155302 | 12/2008 |
| WO | 2009040080 | 4/2009 |
| WO | 2009056614 | 5/2009 |
| WO | 2009070822 | 6/2009 |
| WO | 2006112685 | 12/2010 |

OTHER PUBLICATIONS

The International Search Report and Written Opinion mailed on Apr. 28, 2010 in the corresponding PCT Application No. PCT/KR2009/005906.

The International Search Report and Written Opinion mailed on Jul. 11, 2011 in the related PCT Application No. PCT/ KR2010/007069.

Rostom et al., "Azole antimicrobial pharmacophore-based tetrazoles: Synthesis and biological evaluation as potential antimicrobial and anticonvulsant agents," Bioorganic & Medicinal Chemistry 17 (2009) 2410-2422.

Office Actions mailed on Apr. 19, 2012, May 18, 2012 and Jan. 3, 2012, in related U.S. Appl. No. 12/904,267.

* cited by examiner

SEQUENCE LISTING

<160> NUMBER OF SEQ ID NOS: 8

<210> SEQ ID NO 1
<211> LENGTH: 260
<212> TYPE: PRT
<213> ORGANISM: Oryctolagus cuniculus

<400> SEQUENCE: 1

```
Met Ala Ser Ser Gly Val Thr Arg Arg Asp Pro Leu Ala Asn Lys Val
1               5                   10                  15

Ala Ile Val Thr Ala Ser Thr Asp Gly Ile Gly Leu Ala Ile Ala Arg
            20                  25                  30

Arg Leu Ala Gln Asp Gly Ala His Val Val Ile Ser Ser Arg Lys Gln
        35                  40                  45

Gln Asn Val Asp Arg Ala Val Ala Ala Leu Gln Ala Glu Gly Leu Ser
    50                  55                  60

Val Thr Gly Thr Val Cys His Val Gly Lys Ala Glu Asp Arg Glu Arg
65                  70                  75                  80

Leu Val Ala Thr Ala Leu Asn Leu His Gly Gly Ile Asp Ile Leu Val
                85                  90                  95

Ser Asn Ala Ala Val Asn Pro Phe Phe Gly Lys Leu Met Asp Val Thr
            100                 105                 110

Glu Glu Val Trp Asp Lys Ile Leu Asp Ile Asn Val Lys Ala Met Ala
        115                 120                 125

Leu Met Thr Lys Ala Val Val Pro Glu Met Glu Lys Arg Gly Gly Gly
    130                 135                 140

Ser Val Val Ile Val Ala Ser Ile Ala Ala Phe Asn Pro Phe Ser Gly
145                 150                 155                 160

Leu Gly Pro Tyr Asn Val Ser Lys Thr Ala Leu Val Gly Leu Thr Lys
                165                 170                 175

Asn Leu Ala Leu Glu Leu Ala Ala Gln Asn Ile Arg Val Asn Cys Leu
            180                 185                 190
```

```
Ala Pro Gly Leu Ile Lys Thr Ser Phe Ser Lys Ala Leu Trp Glu Asp
            195                 200                 205

Lys Ala Gln Glu Glu Asn Ile Ile Gln Lys Leu Arg Ile Arg Arg Leu
        210                 215                 220

Gly Lys Pro Glu Glu Cys Ala Gly Ile Val Ser Phe Leu Cys Ser Glu
225                 230                 235                 240

Asp Ala Ser Tyr Ile Thr Gly Glu Thr Val Val Ala Gly Gly Ala
            245                 250                 255

Pro Ser Arg Leu
        260

<210> SEQ ID NO 2
<211> LENGTH: 243
<212> TYPE: PRT
<213> ORGANISM: Candida magnoliae

<400> SEQUENCE: 2

Met Ser Ala Thr Ser Asn Ala Leu Ile Thr Gly Ala Ser Arg Gly Met
1               5                   10                  15

Gly Glu Ala Thr Ala Ile Lys Leu Ala Leu Glu Gly Tyr Ser Val Thr
            20                  25                  30

Leu Ala Ser Arg Gly Ile Glu Gln Leu Asn Ala Ile Lys Glu Lys Leu
        35                  40                  45

Pro Ile Val Lys Lys Gly Gln Gln His Tyr Val Trp Gln Leu Asp Leu
    50                  55                  60

Ser Asp Ile Glu Ala Ala Ser Thr Phe Lys Gly Ala Pro Leu Pro Ala
65                  70                  75                  80

Ser Ser Tyr Asp Val Phe Phe Ser Asn Ala Gly Val Val Asp Phe Ala
                85                  90                  95

Pro Phe Ala Asp Gln Ser Glu Thr Ala Gln Lys Asp Leu Phe Thr Val
            100                 105                 110

Asn Leu Leu Ser Pro Val Ala Leu Thr Lys Thr Ile Val Lys Ala Ile
        115                 120                 125

Ala Asp Lys Pro Arg Glu Thr Pro Ala His Ile Ile Phe Thr Ser Ser
    130                 135                 140

Ile Val Gly Ile Arg Gly Val Pro Asn Val Ala Val Tyr Ser Ala Thr
145                 150                 155                 160

Lys Gly Ala Ile Asp Ser Phe Ala Arg Ser Leu Ala Arg Glu Phe Gly
                165                 170                 175

Pro Lys Asn Ile His Val Asn Cys Val Asn Pro Gly Thr Thr Arg Thr
            180                 185                 190

Glu Met Thr Lys Gly Val Asp Leu Ala Ala Phe Gly Asp Val Pro Ile
        195                 200                 205

Lys Gly Trp Ile Glu Val Asp Ala Ile Ala Asp Ala Val Leu Phe Leu
    210                 215                 220

Ile Lys Ser Lys Asn Ile Thr Gly Gln Ser Leu Val Val Asp Asn Gly
225                 230                 235                 240

Phe Gly Val

<210> SEQ ID NO 3
<211> LENGTH: 241
<212> TYPE: PRT
<213> ORGANISM: Candida vaccinii

<400> SEQUENCE: 3

Met Arg Ser Thr Pro Asn Ala Leu Val Thr Gly Gly Ser Arg Gly Ile
1               5                   10                  15
```

```
Gly Ala Ala Ala Ala Ile Lys Leu Ala Glu Gly Tyr Ser Val Thr
                20                  25                  30
Leu Ala Ser Arg Gly Leu Asp Lys Leu Asn Glu Val Lys Ala Lys Leu
            35                  40                  45
Pro Val Val Lys Gln Gly Gln Glu His His Val Trp Gln Leu Asp Leu
 50                  55                  60
Ser Asp Val Gln Ala Ala Leu Glu Phe Lys Gly Ala Pro Leu Pro Ala
 65                  70                  75                  80
Ser Lys Tyr Asp Leu Phe Val Ser Asn Ala Gly Val Ala Thr Phe Ser
                85                  90                  95
Pro Thr Ala Glu His Asp Asp Lys Asp Trp Gln Asn Ile Ile Ala Val
            100                 105                 110
Asn Leu Thr Ser Pro Ile Ala Ile Thr Lys Ala Leu Val Lys Ala Val
        115                 120                 125
Gly Glu Arg Ser Asn Asp Asn Pro Phe Gln Ile Ala Phe Leu Ser Ser
130                 135                 140
Ala Ala Ala Leu Arg Gly Val Pro Gln Thr Ala Val Tyr Ser Ala Thr
145                 150                 155                 160
Lys Ala Gly Leu Asp Gly Phe Thr Arg Ser Leu Ala Lys Glu Leu Gly
                165                 170                 175
Pro Lys Gly Ile His Val Asn Ile Val His Pro Gly Trp Thr Gln Thr
            180                 185                 190
Glu Met Thr Ala Gly Val Asp Glu Pro Arg Asp Thr Pro Ile Pro Gly
        195                 200                 205
Trp Ile Gln Pro Glu Ala Ile Ala Glu Ala Ile Val Tyr Leu Ala Lys
210                 215                 220
Ser Lys Asn Ile Thr Gly Thr Asn Ile Val Val Asp Asn Gly Leu Thr
225                 230                 235                 240
Ile

<210> SEQ ID NO 4
<211> LENGTH: 239
<212> TYPE: PRT
<213> ORGANISM: Candida magnoliae

<400> SEQUENCE: 4

Met Asn Ala Leu Val Thr Gly Gly Ser Arg Gly Ile Gly Glu Ala Ile
 1               5                  10                  15
Ala Thr Lys Leu Ala Glu Asp Gly Tyr Ser Val Thr Ile Ala Ser Arg
                20                  25                  30
Gly Ile Asp Gln Leu Asn Lys Val Lys Ala Lys Leu Pro Val Val Arg
            35                  40                  45
Glu Gly Gln Thr His His Val Trp Gln Leu Asp Leu Ser Asp Ala Glu
 50                  55                  60
Ala Ala Ser Ser Phe Lys Gly Ala Pro Leu Pro Ala Ser Ser Tyr Asp
 65                  70                  75                  80
Val Leu Val Asn Asn Ala Gly Val Thr Asp Pro Ser Pro Ile Ala Lys
                85                  90                  95
Gln Ser Asp Ser Glu Ile His Lys Leu Phe Ser Val Asn Leu Leu Ser
            100                 105                 110
Pro Val Ala Leu Thr Lys Thr Tyr Val Gln Ala Val Thr Gly Lys Pro
        115                 120                 125
Arg Glu Thr Pro Ala His Ile Ile Phe Ile Ser Ser Gly Val Ala Ile
130                 135                 140
```

```
Arg Gly Tyr Pro Asn Val Ala Val Tyr Ser Ala Thr Lys Ser Gly Leu
145                 150                 155                 160

Asp Gly Phe Met Arg Ser Leu Ala Arg Glu Leu Gly Pro Glu Gly Val
            165                 170                 175

His Val Asn Thr Val Ser Pro Gly Leu Thr Lys Thr Glu Met Ala Ser
        180                 185                 190

Gly Val Ser Leu Asp Asp Phe Pro Pro Ser Pro Ile Gly Gly Trp Ile
    195                 200                 205

Gln Pro Glu Ala Ile Ala Asp Ala Val Arg Tyr Leu Val Lys Ser Lys
    210                 215                 220

Asn Ile Thr Gly Thr Ile Leu Ser Val Asp Asn Gly Ile Thr Val
225                 230                 235
```

<210> SEQ ID NO 5
<211> LENGTH: 780
<212> TYPE: DNA
<213> ORGANISM: Oryctolagus cuniculus

<400> SEQUENCE: 5

| | | |
|---|---|---|
| atggcttcat ctggcgtaac acgccgtgat ccgctggcca acaaagtcgc tattgtcact | 60 |
| gcgtcgaccg atggcatcgg actggcgatt gcgcgtcgcc ttgctcagga cggggctcac | 120 |
| gtggtaatct cttcgcgtaa acagcaaaat gtagatcgtg ccgttgctgc cctgcaagca | 180 |
| gaaggtctgt ccgtaactgg tactgtgtgc catgtcggga agccgagga ccgtgaacgt | 240 |
| ctggttgcga cggcccttaa tcttcatggc ggtatcgata tcctggtgag taacgcggcc | 300 |
| gtcaatccgt ttttcggtaa gttaatggac gtcaccgaag aggtgtggga taaaattctg | 360 |
| gacatcaacg tgaaagcaat ggcgttgatg accaaagcgg tggttccaga atggaaaaa | 420 |
| cgcggtgggg gctcagttgt cattgtgcc agcattgcag cctttaatcc atttagcggc | 480 |
| ttaggtccgt acaatgtgag taaaacggca ttggttggcc tgaccaagaa cctggcattg | 540 |
| gagttagcag cgcagaacat tcgtgttaac tgtttagcgc cgggcctgat taagacatca | 600 |
| ttcagtaagg cactgtggga ggataaagct caggaggaaa atatcattca gaaactgcgt | 660 |
| attcgccgtc tgggaaaacc ggaagaatgt gcaggtatcg ttagctttct gtgctctgaa | 720 |
| gatgcgtcct atattacggg tgaaaccgta gtggttgccg gcggagcgcc gagccgcctg | 780 |

<210> SEQ ID NO 6
<211> LENGTH: 732
<212> TYPE: DNA
<213> ORGANISM: Candida magnoliae

<400> SEQUENCE: 6

| | | |
|---|---|---|
| atgtctgcta cttcgaacgc tcttatcact ggtgccagcc gcggaatggg cgaggccaca | 60 |
| gctattaagc ttgcccttga ggggtacagc gtcacccttg catcacgcgg tattgagcag | 120 |
| ctcaatgcca tcaaggaaaa actacccatc gtgaagaagg ccagcagca ctacgtttgg | 180 |
| cagctcgatc ttagtgacat cgaggcggct tccaccttca agggggctcc tctgcctgcc | 240 |
| agcagctacg acgtgttctt cagcaacgcc ggtgtggtgg actttgctcc gttcgcagac | 300 |
| caaagcgaga ctgcgcaaaa ggacctgttc acggttaacc tgctgtcgcc tgttgcgttg | 360 |
| accaagacca ttgttaaggc catcgccgac aagcccgcg agacgcctgc tcacattatc | 420 |
| ttcacctcgt ccattgtcgg aattcgcggt gttcccaacg tggcggtcta cagcgccacc | 480 |
| aagggcgcga ttgacagctt tgcgcgctcg cttgctcgtg agttcggtcc caagaacatc | 540 |
| cacgttaact gcgtgaaccc gggcacgacg cgcaccgaga tgacaaaggg cgttgatctc | 600 |

```
gcggctttcg gcgatgttcc tatcaagggc tggatcgagg tcgatgcgat tgccgacgct    660
gtgctgtttt tgatcaagtc caagaacatc actggccagt cgctcgttgt tgacaacgga    720
ttcggtgttt aa                                                        732
```

<210> SEQ ID NO 7
<211> LENGTH: 726
<212> TYPE: DNA
<213> ORGANISM: Candida vaccinii

<400> SEQUENCE: 7

```
atgaggtcga cacctaacgc ccttgtgact ggcggcagcc gcggcattgg cgcggccgct     60
gcaattaaac tcgccgaggc aggctacagc gtgacgctcg cgtcgcgcgg tctcgacaag    120
ctcaacgagg tgaaggccaa gcttcctgtc gtgaagcagg ccaggagca ccatgtatgg     180 cagcttgatc tcagcgacgt gcaggccgcg ctcgagttca agggcgcacc gctgccgcg    240 agtaagtacg atttgtttgt ctcgaacgcc ggcgtggcta ctttctcgcc aacggctgag    300
catgacgaca aggactggca gaacattatt gccgtgaact tgacatcgcc cattgccatt    360
acgaaggcgc tcgttaaggc cgttggcgag cgctcaaacg ataacccgtt tcagatcgcg    420
ttcctgtcat cggcggccgc cctgcgcggt gtgccgagga ccgctgttta cagcgctacg    480
aaggccggcc tcgacggctt cacgcgctcg ctcgccaagg agctcggccc aaagggcatc    540
catgtgaaca tcgtacaccc tggatggacg cagaccgaga tgactgcggg tgtagatgag    600
cctagggata cgcccatccc gggctggatc cagccggaag ccatcgccga ggccattgtg    660
tatctcgcga agtcaaagaa catcacggga acgaacatcg ttgtcgacaa cggcctgact    720
atttaa                                                               726
```

<210> SEQ ID NO 8
<211> LENGTH: 720
<212> TYPE: DNA
<213> ORGANISM: Candida magnoliae

<400> SEQUENCE: 8

```
atgaacgctc tagtgaccgg tggtagccgt ggcattggcg aggcgatcgc gaccaagctg     60
gccgaagatg gctacagcgt gacaatcgcc tcgcgcggaa tcgatcagct caacaaggta    120
aaggctaaac ttccggttgt gagggagggc cagacccacc acgtgtggca gcttgatttg    180
agcgacgccg aggccgcgtc gtccttcaag ggcgctcctt tgccagcaag cagctacgat    240
gtccttgtca caacgccgg agtaacggat ccgagtccca ttgcgaagca gtcggatagc    300
gagattcaca agctgtttag cgtgaatctg ctgtcaccag ttgctttgac aaagacgtac    360
gtccaggcgg ttaccggaaa gcctcgtgag acgccagctc acattatttt tatctcgtca    420
ggcgttgcca ttcgaggcta cccaaacgtc gctgtatact cggctactaa gagcgggctc    480
gacggtttca tgaggtctct ggcgcgcgag cttggccccg agggcgtcca tgtgaacact    540
gtcagcccgg gtctcaccaa aaccgagatg gccagcggcg tcagcctcga cgacttcccg    600
ccatcgccga ttgggggctg gatccagccc gaggccatcg ctgatgcagt gaggtacctg    660
gtgaagtcga agaacatcac aggcacgatt ctgtcagttg acaacggaat cacggtttaa    720
```

METHOD FOR PREPARATION OF CARBAMIC ACID (R)-1-ARYL-2-TETRAZOLYL-ETHYL ESTER

RELATED APPLICATIONS

This application claims priority for U.S. Provisional Application No. 61/251,867, filed Oct. 15, 2009, the disclosure of which is incorporated herein in its entirety.

The present invention relates to a method for the preparation of carbamic acid (R)-1-aryl-2-tetrazolyl-ethyl ester. More particularly, the present invention relates to a method for preparing carbamic acid (R)-1-aryl-2-tetrazolyl-ethyl ester, comprising the enantioselective enzyme reduction of an arylketone.

BACKGROUND OF THE INVENTION

As disclosed in U.S. Patent Application Publication No. 2006/0258718 A1, carbamic acid (R)-1-aryl-2-tetrazolyl-ethyl esters (hereinafter referred to as "the carbamate compounds") possess anticonvulsant activity and are useful in the treatment of disorders of the central nervous system, especially including anxiety, depression, convulsion, epilepsy, migraines, bipolar disorder, drug abuse, smoking, ADHD, obesity, sleep disorders, neuropathic pain, strokes, cognitive impairment, neurodegeneration, strokes and muscle spasms.

Depending on the position of N in the tetrazole moiety thereof, the carbamate compounds are divided into two positional isomers: tetrazole-1-yl (hereinafter referred to as "1N tetrazole") and treatzole-2-yl (hereinafter referred to as "2N tetrazole"). The introduction of tetrazole for the preparation of the carbamate compounds results in a 1:1 mixture of the two positional isomers which are required to be individually isolated for pharmaceutical use.

Having chirality, the carbamate compounds must be in high optical purity as well as chemical purity as they are used as medications. In this regard, U.S. Patent Application Publication No. 2006/0258718 A1 uses the pure enantiomer (R)-aryl-oxirane as a starting material, which is converted into an alcohol intermediate through a ring-opening reaction by tetrazole in the presence of a suitable base in a solvent, followed by introducing a carbamoyl group into the resulting alcohol intermediate. For isolation and purification of the 1N and 2N positional isomers thus produced, column chromatography is utilized after the formation of an alcohol intermediate or carbamate.

For use in the preparation described above, (R)-2-aryl-oxirane may be synthesized from an optically active material, such as substituted (R)-mandelic acid derivative via various route, or obtained by asymmetric reduction-ring formation reaction of α-halo arylketone, or by separation of racemic 2-aryl-oxirane mixture into its individual enantiomers. As such, (R)-2-aryl-oxirane is an expensive compound.

In addition, the ring-opening reaction of (R)-2-aryl-oxirane with tetrazole is performed at relatively high temperatures because of the low nucleophilicity of the tetrazole. However, because tetrazoles start to spontaneously degrade at 110~120° C., the ring opening reaction includes the highly likely risk of a runaway reaction.

In terms of a selection of reaction, as there are two reaction sites in each (R)-2-aryl-oxirane and tetrazole, the ring-opening reaction therebetween affords the substitution of 1N- or 2N-tetrazole at the benzyl or terminal position, resulting in a mixture of a total of 4 positional isomers. Therefore, individual positional isomers are low in production yield and difficult to isolate and purify.

SUMMARY OF THE INVENTION

In accordance with the present invention, the foregoing disadvantages of the prior art are overcome by a novel method for preparing carbamic (R)-1-aryl-2-tetrazolyl-ethyl esters. In the present method, a (R)-1-aryl-2-tetrazolyl-ethyl alcohol represented by Chemical Formula 3 is formed by the enantioselective enzymatic reduction of an arylketone, represented by Chemical Formula 2, and the alcohol is then carbamated to form the carbamic acid (R)-1-aryl-2-tetrazolyl ethyl ester, represented by Chemical Formula 1:

[Chemical Formula 1]

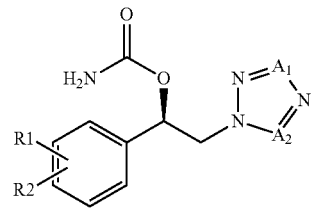

[Chemical Formula 2]

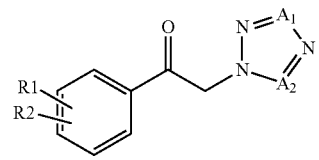

[Chemical Formula 3]

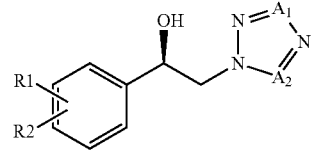

wherein, $R_1$ and $R_2$ are independently selected from a group consisting of hydrogen, halogen, perfluoroalkyl, alkyl of 1 to 8 carbon atoms, thioalkoxy of 1 to 8 carbon atoms, and alkoxy of 1 to 8 carbon atoms; and one of $A_1$ and $A_2$ is CH with the other being N.

DESCRIPTION OF THE PREFERRED EMBODIMENTS

In accordance with an embodiment of the present invention, a method comprising enantioselective enzymatic reduction of an arylketone represented by the following Chemical Formula 2 and the carbamation of the resultant alcohol compound represented by the following Chemical Formula 3 is provided for the preparation of carbamic acid (R)-1-aryl-2-tetrazolyl-ethyl ester, represented by the following Chemical Formula 1.

[Chemical Formula 1]

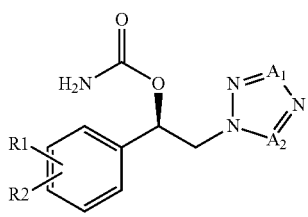

[Chemical Formula 2]

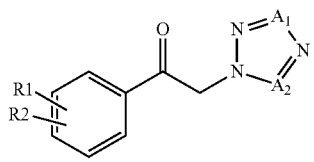

[Chemical Formula 3]

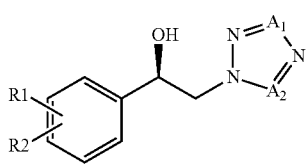

wherein, $R_1$ and $R_2$ are independently selected from a group consisting of hydrogen, halogen, perfluoroalkyl, alkyl of 1 to 8 carbon atoms, thioalkoxy of 1 to 8 carbon atoms, and alkoxy of 1 to 8 carbon atoms; and one of $A_1$ and $A_2$ is CH with the other being N.

The arylketone of Chemical Formula 2, useful as a starting material in the preparation method of the present invention, may be synthesized by, for example, a substitution reaction between the arylketone of Chemical Formula 4 and tetrazole of Chemical Formula 5:

[Chemical Formula 4]

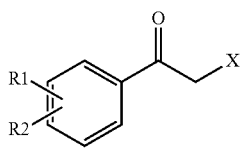

[Chemical Formula 5]

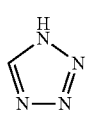

wherein, $R_1$ and $R_2$ are as defined above; and

X is a leaving group, such as a halide or sulfonate.

An economical advantage is given to the synthesis of the arylketones of Chemical Formula 2 from the compounds represented by Chemical Formulae 4 and 5 because they are commercially available, relatively inexpensive compounds. In addition, the substitution reaction can be carried out in relatively mild conditions, compared to the ring-opening reaction between (R)-2-aryl-oxirane and tetrazole. The method according to the present invention is therefore certain of process safety, although employing potentially explosive tetrazole, and ensures high production yield and easy purification, with the production of no unnecessary positional isomers at benzyl positions.

The arylketone represented by Chemical Formula 2 which can be synthesized by the substitution reaction with tetrazole may be in a mixture of positional isomers including 1N arylketone of the following Chemical Formula 2a and 2N arylketone of the following Chemical Formula 2b, which can be isolated and purified through commercially available crystallization.

[Chemical Formula 2a]

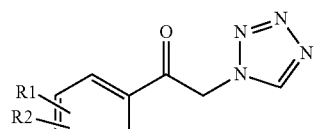

[Chemical Formula 2b]

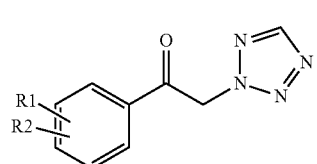

The crystallization useful in the present invention may comprise adding a solubilizing agent to the product of the substitution reaction, that is a mixture of the positional isomers, and then adding a precipitating agent. Optionally, the crystallization may further comprise, after the precipitation, filtrating the precipitate, concentrating the filtrate and adding an additional precipitating agent.

Illustrative, non-limiting examples of the solubilizing agent include acetone, acetonitrile, tetrahydrofuran, ethyl acetate, dichloromethane, chloroform, 1,4-dioxane, and lower alcohols of 1 to 4 carbon atoms, and combinations thereof. The solubilizing agent may be used in an amount of from 0 to 20 ml (v/w) based on the weight (g) of the mixture of the positional isomers. As used herein, the addition of the solubilizing agent in an amount of zero ml (v/w) is intended to mean immediately adding the subsequent precipitating agent without dilution of the filtrate.

Examples of the precipitating agent include water, C1-C4 lower alcohol, diethylether, pentane, hexane, cyclohexane, heptane and combinations thereof, but are not limited thereto. The precipitating agent may be slowly added in an amount of from zero to 40 ml (v/w) based on the weight (g) of the mixture of positional isomers. As used herein, the addition of the precipitating agent in an amount of zero ml is intended to mean allowing the reaction mixture to stand, or cooling it without the addition of the precipitating agent to yield the precipitates. Filtration of the precipitates yields the 1N arylketone of Chemical Formula 2a as crystals with high purity.

On the other hand, the filtrate thus obtained after the filtration step may be concentrated to increase the ratio of the precipitating agent to the solubilizing agent, thereby yielding the 2N arylketone of Chemical Formula 2b with high purity. The concentration ratio of the filtrate can be suitably determined by those of ordinary skill in the art. For example, concentration is carried until the solvent is totally removed off, then the solubilizing agent and the precipitating agent are added as described above. Unlike column chromatography, this crystallization may be commercially used without much difficulty.

The enantioselective enzymatic reduction according to the present invention allows for the conversion of the arylketone of Chemical Formula 2 above into the alcohol compound with (R)-configuration, represented by the Chemical Formula 3 above. The enantioselective enzymatic reduction may be performed using an oxidoreductase enzyme that is in suspension in the reaction mixture, or immobilized in a conventional manner. The enzyme may be utilized in a completely purified state, in a partially purified state, or in the microbial cells is which it was expressed. The cells themselves may be in a native state, a permeabilized state or a lysed state. It will be appreciated by those of ordinary skill in the art that use of the enzyme in the cells is preferred for the practice of the process of the invention since it represents a significant savings in cost. Most preferably, the enzyme is expressed in *E. coli* and used as a suspension of native cells.

The process of enzymatic reduction of the aryl ketone compounds of Formula 2 can be performed in a reaction mixture comprising said compound of Chemical Formula 2, an oxidoreductase, NADH or NADPH as a cofactor, a second substrate and a suitable buffer wherein the oxidoreductase comprises an amino acid sequence wherein at least 60% of the amino acids are identical with one of the amino acid sequences SEQ ID NO: 1, SEQ ID NO: 2, SEQ ID NO: 3 or SEQ ID NO:4.

It has been found that polypeptides comprising one of amino acid sequences SEQ ID NO: 1, SEQ ID NO: 2, SEQ ID NO: 3 or SEQ ID NO:4 or a polypeptides comprising an amino sequence which is identical by at least 60%, preferably at least 90% to one of the amino acid sequences SEQ ID NO: 1, SEQ ID NO: 2, SEQ ID NO: 3 or SEQ ID NO:4 and possessing oxidoreductase activity can be used for reducing the compound of Formula 2 to the compound of Formula 3 (R-configuration) with high conversion and high enantiomeric selectivity. The enantiomeric excess of the R-alcohol formed in the enantioselective enzymatic reduction is at least about 89%, preferably at least about 95% and most preferably at least about 99%.

The organism producing the oxidoreductase polypeptides useful in the enantioselective enzymatic reduction may be a wild strain or a variant and is preferably selected from *Candida magnolia*, *Candida vaccinii*, and *Oryctolagus cuniculus*. Yeast of the *Candida* genus is preferred for producing the oxidoreductase enzymes utilized in the present process. Derivatives of the polypeptides are those having at least sixty percent homology with the SEQ IDs given above and possessing oxidoreductase activity. Those skilled in the art are aware that there are systems and technology available to accurately determine sequence homology.

A polypeptide comprising SEQ ID NO:1 may be encoded by a DNA sequence SEQ ID NO:5 which is obtainable, for example, from the organism *Oryctolagus cuniculus* deposited under the conditions of the Budapest Treaty with the Deutsche Sammlung für Mikroorganismen and Zellkulturen, Mascheroder Weg 1b, 38124 under the number DSMZ 22167, specifically from rabbit DSMZ 22167, or by a nucleic acid sequence that hybridizes therewith. A polypeptide comprising SEQ ID NO:2 may be encoded by a DNA sequence SEQ ID NO:6 which is obtainable, for example, from the organism *Candida magnoliae* DSMZ 22052, or by a nucleic acid sequence that hybridizes therewith.

A polypeptide comprising SEQ ID NO:3 may be encoded by a DNA sequence SEQ ID NO:7, which is obtainable, for example, from the organism *Candida vaccinii* CBS7318, or by a nucleic acid sequence that hybridizes therewith. A polypeptide comprising SEQ ID NO:4 may be encoded by a DNA sequence SEQ ID NO:8, which is obtainable, for example, from the organism *Candida magnoliae* CBS6396, or by a nucleic acid sequence that hybridizes therewith.

The oxidoreductase having one of polypeptide sequences mentioned above is obtained in useable quantities by conventional procedures recognized by those skilled in the art. A polynucleotide coding for the amino acid sequence is cloned into a suitable vector and thereafter introduced into a host organism capable of expressing the gene coding for the sequence. Microorganisms susceptible of transforming to become capable of expressing of such a peptide are well known in the art. A preferred microorganism is *Escherichia coli*. As stated above, the oxidoreductase expressed by transformed *E. coli* may be extracted from the *E. coli* cells and partially or completely purified for use in the process, or may be utilized in the cells themselves which may be in a native, permeabilized or lysed state. A preferred embodiment of the enantioselective enzymatic reduction of the present invention utilizes a suspension of the oxidoreductase as cells in the native state. Any of these forms may be utilized in the free or immobilized form.

The reduction reaction may be carried out in a single phase system having the cells containing the enzyme suspended therein. Alternatively, the reaction may be performed in a two-phase aqueous/organic solvent system as described in U.S. Patent Application Publication No. 2009/0017510 and U.S. Pat. No. 7,371,903. The reaction may be carried out as a conventional batch reaction, or as a continuous process. It will be appreciated that one of the significant advantages of the enantioselective enzymatic reduction for commercial applications is that it is amenable to continuous operation.

The reaction mixture preferably contains from about 35 g to 350 g of cells per kg of reactant added therein. The suspension is the aqueous portion of the reaction mixture which also contains a buffer, for example a TEA (triethanolamine), phosphate, Tris/HCl or glycine buffer. The buffer may additionally comprise ions for the stabilization of the enzyme, for example, a source of magnesium ions. Additional additives that may be present in the buffer for stabilizing the enzymes may include a polyol, such as glycerol, sorbitols and the like, sulfur compounds, such as 1,4-DL-dithiothreitol, glutathione, cysteine or the like, amino acids and peptides, or detergents, such as DMSO. A preferred stabilizer for the enzyme is a polyol, particularly glycerol, which may be present in from about 10% to 80% by weight, preferably about 50% by weight, based on the weight of the cell suspension.

The enantioselective enzymatic reduction process is advantageously carried out using a coupled substrate principle wherein the reaction mixture utilizes a second substrate for the regeneration of the cofactor, or coenzyme, which functions to provide hydrogen for the reduction of the arylketone substrate. The cofactor is preferably nicotineamide adenine dinucleotide phosphate (NADP) or nicotineamide adenine dinucleotide (NAD), which are utilized in the reduced state, i.e. NADPH or NADH, respectively. The cofactor is present in the reaction mixture in a concentration of from about 0.01. mM to 5 mM, preferably 0.05 mM to 0.5 mM. In the reaction, the second substrate functions by being oxidized in the regeneration of the NADPH or NADH cofactor. The second substrate is a secondary alcohol represented by the Formula $R_xR_yCHOH$, wherein $R_x$ represents carbon with x being an integer from 1-10 and $R_y$ represents hydrogen with y being an integer equal to two times the value of x plus two. Examples of suitable second substrates include 2-propanol, 2-butanol 4-methyl-2-pentanol, 2-pentanol, 2-heptanol, 2-octanol and the like. A preferred is second substrate is 2-butanol. The second substrate is present in the reaction mixture in from about 10% to 80% by volume, preferably from about 40% to 60% by volume, most preferably about 50% by volume.

The oxidized cofactor formed during the reduction of the arylketone is regenerated by oxidation of the cosubstate, which also can be catalyzed by the oxidoreductase. Thus, a particular economic advantage of the present process is that the oxidoreductase affects both reduction of the arylketone of Formula 1 and oxidation of the cosubstrate, therefore no further enzyme has to be used for cofactor regeneration. It is also within the scope of the present invention to add another enzyme to the reaction mixture for cofactor regeneration in order to enhance the rate of reduction of the aryl ketone.

In a further embodiment, an organic solvent that is not involved in the regeneration of the cofactor may be added to the reaction mixture and the reduction process carried out in an aqueous organic 2-phase system. Examples of such solvents include, without intended limitation, diethyl ether, tertiary butyl methyl ether, diisopropyl ether, dibutyl ether, ethyl acetate, butyl acetate, heptane, hexane or cyclohexane. Such a solvent may be present in from about 1% to 50% by volume based on the volume of the reaction mixture.

The amount of the arylketone substrate in the reaction mixture is preferably greater than about 0.1% by weight and may be increased to about 50% by weight, with a preferred concentration being from about 5 to 30% by weight. The amount of the substrate will vary depending on the purity thereof since the process may be carried out with the substrate in a purified state or as raw product containing varying amounts and types of impurities. The pH of the reaction mixture after the addition of all components will be in the range of 5 to 10, preferably from 7 to 9, and optimally about pH 8. The enzymatic reduction according to the present invention is carried out at a temperature of from about 10-45° C., preferably from about 20-40° C., most preferably from about 25-35° C.

The enantioselective reduction process is cost-effective and environment-friendly in addition to providing the alcohols of Formula 3 in high yield and very high enantioselectivity. Thus, an alcohol compound with an (R)-configuration of high optical purity can be obtained in the presence of the enzyme under the above-mentioned reaction conditions within from about 12 to 96 hours, preferably from about 24 to 48 hours. During the incubation, the pH of the mixture is maintained within the ranges given above by periodic testing and the addition of a conventional acidic or basic reagents, for example sodium carbonate and sodium hydroxide, respectively. The efficiency of the enantioselective enzymatic reduction can be expressed by the total turnover number (TTN) which is the moles of the chiral alcohol of Formula 2 produced per mole of cofactor used. The TTN of the enantioselective enzymatic reduction is from about $10^2$ to $10^5$, preferably $>10^3$.

When the alcohol compound obtained through the enantioselective enzymatic reduction exists as a positional isomer mixture of 1N alcohol of Chemical Formula 3a and 2N alcohol of Chemical Formula 3b, it can be isolated and purified into individual positional isomers of high purity by crystallization:

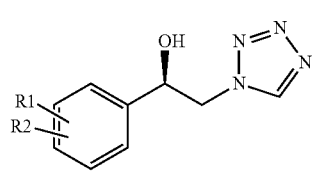

[Chemical Formula 3a]

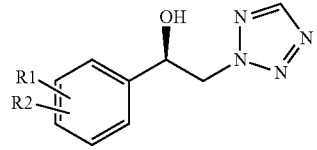

[Chemical Formula 3b]

The crystallization may comprise adding a solubilizing agent to the positional isomer mixture resulting from the reduction; and adding a precipitating agent, and optionally filtering the precipitate; and concentrating the filtrate and adding an additional precipitating agent.

Examples of the solubilizing agent useful in the crystallization include acetone, acetonitrile, tetrahydrofuran, ethyl acetate, dichloromethane, chloroform, 1,4-dioxane, lower alcohol of 1 to 4 carbon atoms, and mixtures thereof, but are not limited thereto. The solubilizing agent may be added in an amount of zero to 20 ml (v/w) based on the weight (g) of the positional isomer mixture.

Non-limiting examples of the precipitating agent include water, a lower alcohol of 1 to 4 carbon atoms, diethylether, pentane, hexane, cyclohexane, heptane, and mixtures thereof. The precipitating agent may be slowly added in an amount of from zero to 40 ml (v/w) based on the weight (g) of the positional isomer mixture.

Following the addition of the precipitating agent, filtration may yield 1N alcohol (3a) as a precipitate of high purity.

Furthermore, 2N alcohol (3b) can be obtained as a crystal form of very high purity by concentrating the filtrate and increasing the ratio of the precipitating agent to the solubilizing agent.

These crystallization steps may be omitted when the positional isomers of arylketone of Chemical Formula 2 are already isolated and purified.

The introduction of a carbomoyl moiety into the alcohol compound with (R)-configuration of Chemical Formula 3 leads to carbamate with (R)-configuration, represented by Chemical Formula 1:

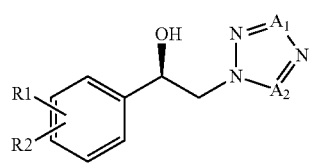

[Chemical Formula 3]

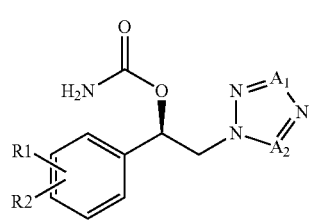

[Chemical Formula 1]

wherein,
$R_1$ and $R_2$ are independently selected from a group consisting of hydrogen, halogen, perfluoroalkyl, an alkyl of 1 to 8 carbon atoms, a thioalkoxy of 1 to 8 carbon atoms, and an alkoxy of 1 to 8 carbon atoms; and one of $A_1$ and $A_2$ is CH with the other being N.

In the carbamation step, for example, inorganic cyanate-organic acid, isocyanate-water, or carbonyl compound-ammonia may be employed to introduce a carbamoyl moiety.

For the carbamation with inorganic cyanate-organic acid, the alcohol compound with (R)-configuration of Chemical Formula 3 is dissolved in an organic solvent, for example, diethylether, tetrahydrofuran, 1,4-dioxane, acetonitrile, dichloromethane, chloroform or mixtures thereof, and mixed with 1 to 4 equivalents of inorganic cyanate such as sodium cyanate and an organic acid, such as methane sulfonic acid or acetic acid, followed by reacting at about −10 to 70° C.

With regard to use of the isocyanate-water, 1 to 4 equivalents of isocyanate, for example, chlorosulfonic isocyanate, trichloroacetyl isocyanate, trimethylsilyl isocyanate, are added to a solution of the alcohol compound with (R)-configuration of Chemical Formula 3 in an organic solvent, for example, diethylether, tetrahydrofuran, 1,4-dioxane, acetonitrile, dichloromethane, chloroform or mixtures thereof, and reacted at about −50 to 40° C. Subsequently, without purification, 1 to 20 equivalents of water are added to induce hydrolysis.

With regard to use of the carbonyl compound-ammonia, 1 to 4 equivalents of a carbonyl compound, for example, 1,1'-carbonyldiimidazole, carbamoly chloride, N N-disuccinimidyl disuccinimidyl carbonate phosgene, triphosgene, or chloroformate, are added to a solution of the alcohol compound with (R)-configuration of Chemical Formula 3 in an organic solvent, for example, diethylether, tetrahydrofuran, 1,4-dioxane, acetonitrile, dichloromethane, chloroform or mixtures thereof, and reacted at about −10 to 70° C., followed by adding 1 to 10 equivalents of ammonia without purification.

After the carbamation, the carbamate compound of Chemical Formula 1 thus obtained may be purified to higher optical and chemical purity through the following crystallization. The crystallization comprises adding a solubilizing agent to the product of the carbamation; and then adding a precipitating agent, and optionally filtering the precipitate and adding an additional precipitating agent. For pharmaceutical use, it is preferable that there is always a final purification of the carbamated product before use, but that there can be a crystallization step earlier in the process.

Non-limiting examples of the solubilizing agent include acetone, acetonitrile, tetrahydrofuran, ethyl acetate, dichloromethane, chloroform, 1,4-dioxane, lower alcohol of 1 to 4 carbon atoms, and mixtures thereof. Based on the weight (g) of the reaction product, the solubilizing agent may be used in an amount of from zero to 20 ml (v/w).

Non-limiting examples of the precipitating agent include water, lower alcohols of 1 to 4 carbon atoms, diethylether, pentane, hexane, cyclohexane, heptane and mixtures thereof. Based on the weight (g) of the reaction product, the precipitating agent may be slowly added in an amount of from zero to 40 ml (v/w).

Comprising enantioselective enzymatic reduction, the method of the present invention can provide optically high pure carbamate compounds. In addition, the mild reaction conditions which the method of the present invention requires ensure process safety. Furthermore, the crystallization step applicable to large-scale production before or after the enantioselective enzymatic reduction or after the carbamation results in a higher chemical purity of the carbamate compounds. The carbamate compounds prepared according to the present invention are very useful in the treatment of CNS disorders such as convulsion.

A better understanding of the present invention may be obtained through the following examples which are set forth to illustrate, but are not to be construed as in any way limiting the present invention.

Preparation Example 1

Preparation of 1-(2-chlorophenyl)-2-(1,2,3,4-tetrazol-1-yl)ethan-1-one

To a suspension of 2-bromo-2'-chloroacetophenone (228.3 g, 0.978 mol) and potassium carbonate (161.6 g, 1.170 mol) in acetonitrile (2000 mL) was added a 35 w/w % 1H-tetrazole dimethylformamide solution (215.1 g, 1.080 mol) at room temperature. These reactants were stirred for 2 h at 45° C. and distilled under reduced pressure to remove about 1500 mL of the solvent. The concentrate was diluted in ethyl acetate (2000 mL) and washed with 10% brine (3×2000 mL). The organic layer thus separated was distilled under reduced pressure to afford 216.4 g of an oily solid residue. To a solution of the solid residue in ethyl acetate (432 mL) was slowly added heptane (600 mL). The precipitate thus formed was filtered at room temperature and washed to yield 90.1 g (0.405 mol) of 1-(2-chlorophenyl)-2-(1,2,3,4-tetrazol-1-yl)ethan-1-one (hereinafter referred to as "1N ketone").

$^1$H-NMR (CDCl$_3$)δ8.87 (s, 1H), d7.77 (d, 1H), d7.39-7.62 (m, 3H), d5.98 (s, 2H)

Preparation Example 2

Preparation of 1-(2-chlorophenyl)-2-(1,2,3,4-tetrazol-2-yl)ethan-1-one

After the filtration of Preparation Example 1, the filtrate was concentrated and dissolved in isopropanol (100 mL), and to which heptane (400 mL) was then added to complete the crystallization. Filtering and washing at 5° C. afforded 1-(2-chlorophenyl)-2-(1,2,3,4-tetrazol-2-yl)ethan-1-one (hereinafter referred to as "2N ketone") as a solid. 94.7 g (0.425 mol).

$^1$H-NMR (CDCl$_3$) d8.62 (s, 1H), d7.72 (d, 1H), d7.35-7.55 (m, 3H), d6.17 (s, 2H)

Preparation Example 3

Preparation of Alcohol Compound of (R)-Configuration by Enantioselective Enzymatic Reduction Via Various Oxidoreductases The following four solutions were prepared as follows:
Enzyme Solution 1

Competent *Escherichia coli* StarBL21(De3) cells (Invitrogen) were transformed with the expression constructs pET21-MIX coding for oxidoreductase SEQ ID NO 1. The *Escherichia coli* colonies transformed with the resulting expression constructs were then cultivated in 200 mL of LB medium (1% tryptone, 0.5% yeast and 1% sodium chloride) with 50 micrograms/mL of ampicillin or 40 micrograms/mL of kanamycin, respectively, until an optical density of 0.5, measured at 550 nm, was achieved. The expression of the desired recombinant protein was induced by the addition of isopropylthiogalactoside (IPTG) to a concentration of 0.1 mM. After 16 hours of induction at 25° C. and 220 rpm, the cells were harvested and frozen at −20° C. In the preparation of the enzyme solutions, 30 g of cells were resuspended in 150 mL of triethanolamine buffer (TEA 100 nM, 2 mM MgCl2, 10% glycerol, pH 8) and homogenized in a high pressure homogenizer. The resultant enzyme solution was mixed with 150 mL glycerol and stored at −20° C.

Enzyme Solution 2

RB791 cells (*E. coli* genetic stock, Yale, USA) were transformed with the expression constructs pET21-MIX coding for oxidoreductase SEQ ID NO 2. The *Escherichia coli* colonies transformed with the resulting expression constructs were then cultivated in 200 mL of LB medium (1% tryptone, 0.5% yeast and 1% sodium chloride) with 50 micrograms/mL of ampicillin or 40 micrograms/mL of kanamycin, respectively, until an optical density of 0.5, measured at 550 nm, was achieved. The expression of the desired recombinant protein was induced by the addition of isopropylthiogalactoside (IPTG) to a concentration of 0.1 mM. After 16 hours of induction at 25° C. and 220 rpm, the cells were harvested and frozen at −20° C. In the preparation of the enzyme solutions, 30 g of cells were resuspended in 150 mL of triethanolamine buffer (TEA 100 nM, 2 mM MgCl2, 10% glycerol, pH 8) and homogenized in a high pressure homogenizer. The resultant enzyme solution was mixed with 150 mL glycerol and stored at −20° C.

Enzyme Solution 3

Enzyme solution 3 was prepared in the same manner as described in Enzyme solution 1 except that expression constructs pET21-MIX coding for oxidoreductase SEQ ID NO 3 instead of expression constructs pET21-MIX coding for oxidoreductase SEQ ID NO 1 was used.

Enzyme Solution 4

Enzyme solution 4 was prepared in the same manner as described for enzyme solution 2 except that expression constructs pET21-MIX coding for oxidoreductase SEQ ID NO 4 instead of expression constructs pET21-MIX coding for oxidoreductase SEQ ID NO 2 was used.

Different oxidoreductases contained in each of enzyme solutions 1 to 4 were examined as follows for the conversion of 1-(2-chlorophenyl)-2-(1,2,3,4-tetrazol-1-yl)ethan-1-one (1N ketone) and 1-(2-chlorophenyl)-2-(1,2,3,4-tetrazol-1-yl)ethan-1-one (2N ketone) to the corresponding 1-(2-chlorophenyl)-2-(1,2,3,4-tetrazol-1-yl)ethan-1-ol (hereinafter, referred to as "1N alcohol") and 1-(2-chlorophenyl)-2-(1,2,3,4-tetrazol-2-yl)ethan-1-ol (hereinafter, referred to as "2N alcohol"), respectively.

Reaction Batch A

| 160 μl | buffer (TEA 100 nM, 2 mM MgCl2, 10% glycerol, pH 8) |
| 100 μl | NADPH (40 mg/ml) |
| 40 μl | 2-propanol |
| 50 μl | enzyme solution 1 |
| 2 mg | 1N ketone or 2N ketone |

Reaction Batch B

| 160 μl | buffer (TEA 100 nM, 2 mM MgCl2, 10% glycerol, pH 8) |
| 100 μl | NADPH (40 mg/ml) |
| 40 μl | 2-propanol |
| 50 μl | enzyme solution 2 |
| 2 mg | 1N ketone or 2N ketone |

Reaction Batch C

| 350 μl | buffer (TEA 100 nM, 2 mM MgCl2, 10% glycerol, pH 8) |
| 0.05 mg | NADP |
| 50 μl | enzyme solution 3 |
| 10 mg | 1N ketone or 2N ketone |
| 250 μl | 4-methyl-2-pentanol |
| 50 μl | enzyme (oxidoreductase from *Thermoanerobium brockii*) solution for regeneration of cofactor |

Reaction Batch D

| 350 μl | buffer (TEA 100 nM, 2 mM MgCl2, 10% glycerol, pH 8) |
| 0.05 mg | NADP |
| 50 μl | enzyme solution 4 |
| 10 mg | 1N ketone or 2N ketone |
| 250 μl | 4-methyl-2-pentanol |
| 50 μl | enzyme (oxidoreductase from *Thermoanerobium brockii*) solution for regeneration of cofactor |

After 24 h of incubating each reaction batch A, B, C and D, 1 mL of acetonitrile was added to each reaction batch which was centrifuged and transferred into a HPLC analysis vessel for enantiomeric excess and conversion. Conversion and ee-value of products are listed in Table 1 below calculated using the following equations:

$$\text{Conversion Rate (\%)} = [(\text{Area of Product})/(\text{Area of Reactant} + \text{Area of Product})] \times 100$$

$$\text{ee-value (\%)} = [(\text{Area of }R\text{-Configuration} - \text{Area of }S\text{-Configuration})/(\text{Area of }R\text{-Configuration} + \text{Area of }S\text{-Configuration})] \times 100$$

TABLE 1

| Reaction batch used | Conversion (% of reduced ketone) | ee-values % ee(enantiomer) R-2N Alcohol, 2b | R-1N Alcohol, 2a |
|---|---|---|---|
| Reaction batch A | >98 | 89(R) | >99(R) |
| Reaction batch B | >98 | >99(R) | >99(R) |
| Reaction batch C | >98 | 95(R) | >99(R) |
| Reaction batch D | >98 | 98(R) | 95(R) |

Preparation Example 4

Enzymatic Reduction Via Oxidoreductase SEQ NO: 2

For the conversion of 1N/2N ketone to R-1N/R-2N alcohol, 30 μl of the enzyme solution 2 containing the oxidoreductase SEQ NO: 2 were added to a mixture of 300 μl of a buffer (100 mM TEA, pH 8, 1 mM MgCl2, 10% glycerol), 100 mg of a mixture of 1N ketone and 2N ketone (1N:2N=14%:86%), 0.04 mg NADP and 300 μl 2-butanol. The reaction mixture was incubated at room temperature under constant thorough mixing. After 48 hours, more than 98% of the ketones were reduced to an alcohol mixture of the following composition (R-2N alcohol 80%; S-2N alcohol 0%; R-1N alcohol 20%, S-1N alcohol 0%; 1N ketone 0%; 2N ketone 0%).

After general work up and recrystallization with ethyl acetate/hexane, optically pure alcohols were obtained as below:

(R)-1-(2-chlorophenyl)-2-(1,2,3,4-tetrazol-1-yl)ethan-1-ol (1N alcohol)

$^1$H-NMR (CDCl$_3$) d8.74 (s, 1H), d7.21-7.63 (m, 4H), d5.57 (m, 1H), d4.90 (d, 1H), d4.50 (d, 1H), d3.18 (d, 1H);

(R)-1-(2-chlorophenyl)-2-(1,2,3,4-tetrazol-2-yl)ethan-1-ol (2N alcohol)

$^1$H-NMR (CDCl$_3$) d8.55 (s, 1H), d7.28-7.66 (m, 4H), d5.73 (d, 1H), d4.98 (d, 1H), d4.83 (d, 1H), d3.38 (br, 1H).

Preparation of Carbamate

Preparation Example 5

Preparation of Carbamic Acid (R)-1-(2-Chlorophenyl)-2-(tetrazol-2-yl)ethyl ester 50 ml of the enzyme solution 2 containing the oxidoreductase SEQ NO: 2 were added to a mixture of 250 ml of a buffer (100 mM TEA, pH 8, 1 mM MgCl2, 10% glycerol), 50 g (225 mmol) of 1-(2-chlorophenyl)-2-(1,2,3,4-tetrazol-2-yl)ethan-1-one (2N ketone), 4 mg NAD, 300 ml of 2-propanol and 150 mL of butyl acetate. The reaction mixture was stirred at room temperature. After 48 hours more than 98% of 2N ketone was reduced to corresponding (R)-1-(2-chlorophenyl)-2-(1,2,3,4-tetrazol-2-yl)ethan-1-ol (R-2N alcohol) with >99% ee values. To this resulting mixture, 500 mL of ethyl acetate was added. After being separated, the organic layer thus formed was washed with 10% brine (3×500 mL). The organic layer thus formed was dried over magnesium sulfate and filtered and the filtrate was distilled under reduced pressure to give 50.4 g (224 mmol) of 1-(2-chlorophenyl)-2-(1,2,3,4-tetrazol-2-yl)ethan-1-ol (R-2N alcohol, optical purity 99.9%) as an oily residue. To this resulting crude product, 450 mL of tetrahydrofuran was added. After cooling to −15° C., 38 g (267 mmol) of chlorosulfonyl isocyanate was slowly added and stirred at −10° C. for 2 h. The slow addition of water induced termination of the reaction. The resulting solution was concentrated under reduced pressure until about 300 mL of the solvent was removed. The concentrate was diluted with 600 mL of ethyl acetate and washed with 10% brine (3×500 mL). The organic layer was concentrated under reduced pressure and the concentrate was dissolved in isopropanol (90 mL) to which heptane (180 mL) was slowly added, leading to the completion of crystallization. The precipitate thus obtained was filtered and washed to afford 51.8 g (194 mmol) of carbamic acid (R)-1-(2-chlorophenyl)-2-(tetrazol-2-yl)ethyl ester (optical purity 99.9%).

$^1$H-NMR (Acetone-$d_6$) d8.74 (s, 1H), d7.38-7.54 (m, 4H), d6.59 (m, 1H), d6.16 (Br, 2H), d4.90 (d, 1H), d5.09 (m, 2H)

As described hitherto, carbamate compounds with high optical and chemical purity can be produced with an economical benefit in accordance with the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Amino Acid Sequences

```
SEQ ID NO 1: Oryctolagus cuniculus from rabbit DSMZ 22167
  1 massgvtrrd plankvaivt astdgiglai arrlaqdgah vvissrkqqn vdravaalqa 61 eglsvtgtvc hvgkaedrer lvatalnlhg gidilvsnaa vnpffgklmd vteevwdkil 121 dinvkamalm tkavvpemek rgggsvviva siaafnpfsg lgpynvskta lvgltknlal 181 elaaqnirvn clapglikts fskalwedka qeeniiqklr irrlgkpeec agivsflcse 241 dasyitgetv vvaggapsrl SEQ ID NO 2: Candida magnoliae DSMZ 22052 protein sequence carbonyl reductase
  1 msatsnalit gasrgmgeat aiklalegys vtlasrgieq lnaikeklpi vkkgqqgyvw 61 qldlsdieaa stfkgaplpa ssydvffsna gvvdfapfad qsetaqkdlf tvnllspval 121 tktivkaiad kpretpahii ftssivgirg vpnvavysat kgaidsfars larefgpkni 181 hvncvnpgtt rtemtkgvdl aafgdvpikg wievdaiada vlfliskni tgqslvvdng 241 fgv SEQ ID NO 3: Candida vaccinii CBS7318 protein sequence carbonyl reductase
  1 mrstpnalvt ggsrgigaaa aiklaeagys vtlasrgldk lnevkaklpv vkqgqehhvw 61 qldlsdvqaa lefkgaplpa skydlfvsna gvatfsptae hddkdwqnii avnltspiai 121 tkalvkavge rsndnpfqia flssaaalrg vpqtavysat kagldgftrs lakelgpkgi 181 hvnivhpgwt qtemtagvde prdtpipgwi qpeaiaeaiv ylaksknitg tnivvdnglt 241 i SEQ ID NO 4: Candida magnoliae CBS6396 protein sequence carbonyl reductase
  1 mnalvtggsr gigeaiatkl aedgysvtia srgidqlnkv kaklpvvreg qthhvwqldl 61 sdaeaassfk gaplpassyd vlvnnagvtd pspiakqsds eihklfsvnl lspvaltkty 121 vqavtgkpre tpahiifiss gvairgypnv avysatksgl dgfmrslare lgpegvhvnt 181 vspgltktem asgvslddfp pspiggwiqp eaiadavryl vksknitgti lsvdngitv
```

Nucleic Acid Sequences

SEQ ID NO 5: *Oryctolagus cuniculus* from rabbit DSMZ 22167
```
  1 atggcttcat ctggcgtaac acgccgtgat ccgctggcca acaaagtcgc tattgtcact
 61 gcgtcgaccg atggcatcgg actggcgatt gcgcgtcgcc ttgctcagga cggggctcac
121 gtggtaatct cttcgcgtaa acagcaaaat gtagatcgtg ccgttgctgc cctgcaagca
181 gaaggtctgt ccgtaactgg tactgtgtgc catgtcggga aagccgagga ccgtgaacgt
241 ctggttgcga cggcccttaa tcttcatggc ggtatcgata tcctggtgag taacgcggcc
301 gtcaatccgt ttttcggtaa gttaatggac gtcaccgaag aggtgtggga taaaattctg
361 gacatcaacg tgaaagcaat ggcgttgatg accaaagcgg tggttccaga aatggaaaaa
421 cgcggtgggg gctcagttgt cattgtggcc agcattgcag cctttaatcc atttagcggc
481 ttaggtccgt acaatgtgag taaaacggca ttggttggcc tgaccaagaa cctggcattg
541 gagttagcag cgcagaacat tcgtgttaac tgtttagcgc cgggcctgat taagacatca
601 ttcagtaagg cactgtggga ggataaagct caggaggaaa atatcattca gaaactgcgt
661 attcgccgtc tgggaaaacc ggaagaatgt gcaggtatcg ttagctttct gtgctctgaa
721 gatgcgtcct atattacggg tgaaaccgta gtggttgccg gcggagcgcc gagccgcctg
```

SEQ ID NO 6: *Candida magnolias* DSMZ 22052 nucleic acid sequence carbonyl reductase
```
  1 atgtctgcta cttcgaacgc tcttatcact ggtgccagcc gcggaatggg cgaggccaca
 61 gctattaagc ttgcccttga ggggtacagc gtcacccttg catcacgcgg tattgagcag
121 ctcaatgcca tcaaggaaaa actacccatc gtgaagaagg ccagcagca ctacgtttgg
181 cagctcgatc ttagtgacat cgaggcggct tccaccttca aggggctcc tctgcctgcc
241 agcagctacg acgtgttctt cagcaacgcc ggtgtggtgg actttgctcc gttcgcagac
301 caaagcgaga ctgcgcaaaa ggacctgttc acggttaacc tgctgtcgcc tgttgcgttg
361 accaagacca ttgttaaggc catcgccgac aagccccgcg agacgcctgc tcacattatc
421 ttcacctcgt ccattgtcgg aattcgcggt gttcccaacg tggcggtcta cagcgccacc
481 aagggcgcga ttgacagctt tgcgcgctcg cttgctcgtg agttcggtcc caagaacatc
541 cacgttaact gcgtgaaccc gggcacgacg cgcaccgaga tgacaaaggg cgttgatctc
601 gcggctttcg gcgatgttcc tatcaagggc tggatcgagg tcgatgcgat tgccgacgct
661 gtgctgtttt tgatcaagtc caagaacatc actggccagt cgctcgttgt tgacaacgga
721 ttcggtgttt aa
```

SEQ ID NO 7: *Candida vaccinii* CBS7318 nucleic acid sequence carbonyl reductase
```
  1 atgaggtcga cacctaacgc ccttgtgact ggcggcagcc gcggcattgg cgcggccgct
 61 gcaattaaac tcgccgaggc aggctacagc gtgacgctcg cgtcgcgcgg tctcgacaag
121 ctcaacgagg tgaaggccaa gcttcctgtc gtgaagcagg ccaggagca ccatgtatgg
181 cagcttgatc tcagcgacgt gcaggccgcg ctcgagttca agggcgcacc gctgcccgcg
241 agtaagtacg atttgtttgt ctcgaacgcc ggcgtggcta ctttctcgcc aacggctgag
301 catgacgaca aggactggca gaacattatt gccgtgaact tgacatcgcc cattgccatt
361 acgaaggcgc tcgttaaggc cgttggcgag cgctcaaacg ataacccgtt tcagatcgcg
421 ttcctgtcat cggcggccgc cctgcgcggt gtgccgcaga ccgctgttta cagcgctacg
481 aaggccggcc tcgacggctt cacgcgctcg ctcgccaagg agctcggccc aaagggcatc
541 catgtgaaca tcgtacaccc tggatggacg cagaccgaga tgactgcggg tgtagatgag
601 cctagggata cgcccatccc gggctggatc cagccggaag ccatcgccga ggccattgtg
```

-continued

```
661 tatctcgcga agtcaaagaa catcacggga acgaacatcg ttgtcgacaa cggcctgact 721 atttaa
```

SEQ ID NO 8: *Candida magnoliae* CBS6396 nucleic acid sequence carbonyl reductase

```
  1 atgaacgctc tagtcaccgg tggtagccgt ggcattggcg aggcgatcgc gaccaagctg 61 gccgaagatg gctacagcgt gacaatcgcc tcgcgcggaa tcgatcagct caacaaggta 121 aaggctaaac ttccggttgt gagggagggc cagacccacc acgtgtggca gcttgatttg 181 agcgacgccg aggccgcgtc gtccttcaag gcgctccttt gccagcaag cagctacgat 241 gtccttgtca caacgccgg agtaacggat ccgagtccca ttgcgaagca gtcggatagc 301 gagattcaca agctgtttag cgtgaatctg ctgtcaccag ttgctttgac aaagacgtac 361 gtccaggcgg ttaccggaaa gcctcgtgag acgccagctc acattatttt tatctcgtca 421 ggcgttgcca ttcgaggcta cccaaacgtc gctgtatact cggctactaa gagcgggctc 481 gacggtttca tgaggtctct ggcgcgcgag cttggccccg agggcgtcca tgtgaacact 541 gtcagcccgg gtctcaccaa aaccgagatg gccagcggcg tcagcctcga cgacttcccg 601 ccatcgccga ttggggggctg gatccagccc gaggccatcg ctgatgcagt gaggtacctg 661 gtgaagtcga agaacatcac aggcacgatt ctgtcagttg acaacggaat cacggtttaa
```

---

What is claimed is:

1. A method for preparing carbamic acid aryl-2-tetrazoyl ethyl ester of the Chemical Formula 1, comprising:
subjecting an arylketone of the Chemical Formula 2, to enantioselective enzymatic reduction in a reaction mixture comprising said compound, an oxidoreductase having at least 90% homology with amino acid sequence SEQ ID NO: 2, NADH or NADPH as a cofactor that is oxidized during the reduction process and continuously regenerated, a second substrate comprising a secondary alcohol having the Formula RR'CHOH, wherein R and R' are independent from one another and have from 1 to 10 carbon atoms, and a suitable buffer to form an alcohol compound of (R)-configuration, of Chemical Formula 3; and carbamating said alcohol

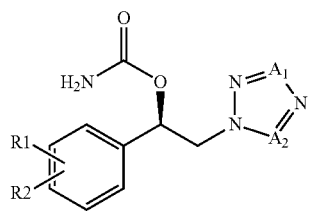
[Chemical Formula 1]

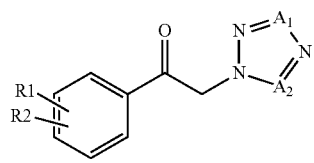
[Chemical Formula 2]

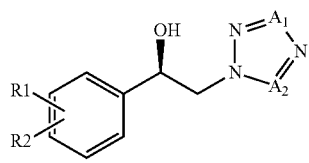
[Chemical Formula 3]

wherein, $R_1$ and $R_2$ are independently selected from the group consisting of hydrogen, halogen, perfluoroalkyl, an alkyl of 1 to 8 carbon atoms, a thioalkoxy of 1 to 8 carbon atoms, and an alkoxy of 1 to 8 carbon atoms; and one of $A_1$ and $A_2$ is CH with the other being N.

2. The method according to claim 1, wherein the oxidoreductase is encoded by nucleic acid sequence SEQ ID NO: 6.

3. The method according to claim 2, wherein the oxidoreductase is isolated from *Candida magnolia, Candida vaccinii* or *Oryctolagus cuniculus*.

4. The method according to claim 1, wherein the oxidoreductase is purified or in a microbial cell.

5. The method according to claim 1, wherein the oxidoreductase is partially purified.

6. The method according to claim 1, wherein the oxidoreductase is a microbial cell lysate.

7. The method according to claim 4, wherein the oxidoreductase is present in the microbial cells and is permeabilized.

8. The method according to claim 7, wherein the microbial cells are transformed *Escherichia coli* cells.

9. The method according to claim 1, wherein the regeneration of the oxidized cofactor results from the oxidation of said second substrate.

10. The method according to claim 1, wherein said second substrate is a secondary alcohol selected from the group consisting of 2-propanol, 2 butanol, 2-pentanol, 4-methyl-2-pentanol, 2-heptanol and 2-octanol.

11. The method according to claim 1, wherein said oxidoreductase affects both the reduction of the arylketone of Formula 2 and the oxidation of the second substrate.

12. The method according to claim 1, wherein the carbamating step comprises reacting the alcohol compound of (R)-configuration of Chemical Formula 3 with inorganic cyanate and an organic acid.

13. The method according to claim 1, wherein the carbamating step comprises hydrolyzing a product resulting from the reaction between the alcohol compound of (R)-configuration of Chemical Formula 3 and an isocyanate compound selected from the group consisting of chlorosulfonic isocyanate, trichloroacetyl isocyanate and trimethylsilyl isocyanate.

14. The method according to claim 1, wherein the carbamating step comprises introducing ammonia into a product resulting from the reaction between the alcohol compound of (R)-configuration of Chemical formula 3 and a carbonyl compound comprising 1,1'-carbonyldiimidazole, carbamoylhalide, N,N-disuccinimidyl carbonate, phosgene, triphosgene or chloroformate.

15. The method according to claim 1, further comprising crystallizing the compound of Formula 1.

16. The method according to claim 15, wherein the crystallizing step comprises:

adding to a reaction product a solubilizing agent selected from the group consisting of acetone, acetonitrile, tetrahydrofuran, ethyl acetate, dichloromethane, chloroform, 1,4-dioxane, an alcohol of 1 to 4 carbon atoms and mixtures thereof; and adding a precipitating agent thereto selected from the group consisting of water, an alcohol of 1 to 4 carbon atoms, diethylether, pentane, hexane, cyclohexane, heptane and mixtures thereof.

17. The method according to claim 1, additionally including the step of preparing the arylketone of Chemical Formula 2 by a substitution reaction between an arylketone of the following Chemical Formula 4 and a tetrazole of the following Chemical Formula 5:

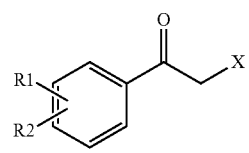
[Chemical Formula 4]

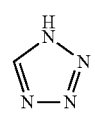
[Chemical Formula 5]

wherein, $R_1$ and $R_2$ are as defined in claim 1; and

X is a leaving group selected from among halides and sulfonates.

18. A method according to claim 17, further comprising a crystallizing step comprising:

adding a solubilizing agent selected from the group consisting of acetone, acetonitrile, tetrahydrofuran, ethyl acetate, dichloromethane, chloroform, 1,4-dioxane, an alcohol of 1 to 4 carbon atoms and mixtures thereof to a product obtained by the substitution reaction; and adding a precipitating agent selected from the group consisting of water an alcohol of 1 to 4 carbon atoms, diethylether, pentane, hexane, cyclohexane, heptanes and mixtures thereof.

19. A method for preparing an alcohol compound of the Chemical Formula 3, through the enantioselective enzymatic reduction of an arylketone- of the Chemical Formula 2:

[Chemical Formula 2]

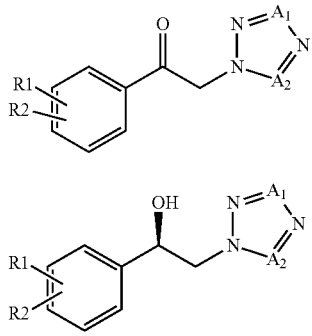

[Chemical Formula 3]

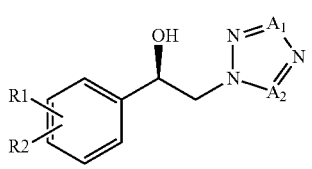

wherein, $R_1$, and $R_2$ are independently selected from a group consisting of hydrogen, halogen, perfluoroalkyl, an alkyl of 1 to 8 carbon atoms, a thioalkoxy of 1 to 8 carbon atoms, and an alkoxy of 1 to 8 carbon atoms;

one of $A_1$ and $A_2$ is CH with the other being N; and said reduction is carried out in a reaction mixture comprising said compound of formula 1, an oxidoreductase having at least 90% homology with amino acid sequence SEQ ID NO: 2, NADH or NADPH as a cofactor is oxidized during the reduction process and continuously regenerated, a second substrate comprising a secondary alcohol having the Formula RR'CHOH, wherein R and R' are independent from one another and have from 1 to 10 carbon atoms, and a suitable buffer.

20. The method according to claim 19, wherein the oxidoreductase is encoded by nucleic acid sequence SEQ ID NO: 6.

21. The method according to claim 19, wherein the oxidoreductase is isolated from *Candid magnolia, Candida vaccinii* or *Oryctolagus cuniculus*.

* * * * *